United States Patent
Ledley et al.

(10) Patent No.: US 6,191,257 B1
(45) Date of Patent: *Feb. 20, 2001

(54) NATURAL OR RECOMBINANT DNA BINDING PROTEINS AS CARRIERS FOR GENE TRANSFER OR GENE THERAPY

(75) Inventors: Fred D. Ledley, Houston, TX (US); Jozsef Stankovics, Pecs (HU)

(73) Assignee: Baylor College of Medicine, Houston, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/480,935

(22) Filed: Jun. 7, 1995

Related U.S. Application Data (63) Continuation of application No. 08/054,493, filed on Apr. 27, 1993, now abandoned.

(51) Int. Cl.$^7$ .............................. C07H 21/04; C07K 14/00

(52) U.S. Cl. ......................................... 530/350; 536/23.1

(58) Field of Search .................................. 514/44, 2, 12; 530/387.3, 350; 536/23.1; 435/172.3, 317.1, 6; 935/52, 111

(56) References Cited

U.S. PATENT DOCUMENTS

| | | | |
|---|---|---|---|
| 4,237,224 | 12/1980 | Cohen et al. | 435/68 |
| 4,740,470 | 4/1988 | Cohen et al. | 435/6 |
| 4,981,784 | * 1/1991 | Evans et al. | 435/6 |
| 5,283,173 | * 2/1994 | Fields et al. | 435/6 |

FOREIGN PATENT DOCUMENTS

| | | |
|---|---|---|
| 90/04788 | 5/1990 | (WO) . |
| 9221752 | 12/1992 | (WO) . |

OTHER PUBLICATIONS

Wagner et al., Proc. Natl. Acad. Sci. 87 : 3410–31 (1990).*
Hutchens et al. (a), Pediatric Research 26(6): 618–622(1989).*
Hutchens et al. (b), Biochem. Biophy. Acta 999 : 323–329 (1989).*
Morrison, Science 229 : 1202–1207 (1985).*
Stowell et al., Biochem. J. 276 : 349–355 (1991).*
Hollenbaugh et al., Curr. Opin. Immunol. 4(2): 216–219 Apr. 1992.*
Sandhu, Critical Reviews in Biotechnology 12(5/6) : 437–462 (1992).*
Lubert Stryer, "Protein Structure and Function", Biochemistry, Chapter 2:31–32 (1988).

Bert O'Malley, "The Steroid Receptor Superfamily: More Excitement Predicted for the Future", Molecular Endocrinology 4:363–369 (1990).
Johnson, et al., "Eukaryotic Transcriptional Regulatory Proteins", Ann. Rev. Biochem 58:799–839 (1989).
Lohman, et al., "Thermodynamic Methods for Model–Independent Determination of Equilibrium Binding Isotherms for Protein–DNA Interactions: Spectroscopic Approaches to Monitor Binding", Meth. Enzymology 208:258–290 (1991).
Patent Abstracts of Japan vol. 163, No. 51 (C–0968) Jul. 29, 1992 and JP,a,04 108 390 (Snow Brand Milk Prod. Co. Ltd.) 1992.
J. Biol. Chem., 268:6866–6869 (1993), S.H. Michael et al.: "Binding–incompetent Adenovirus Facilitates Molecular Conjugate–mediated Gene Transfer by the Receptor–mediates Endocytosis Pathway".
J. Biol. Chem., 264:16985–16987 (1989), C.Y. Wu et al.: "Targeting Genes: Delivery and Persistent Expression of a Foreign Gene Driven by Mammalian Regulatory Elements In Vivo".
Am. J. Respir. Cell Mol. Biol., 6:247–252 (1992), D.T. Curiel et al.: "Gene Transfer to Respiratory Epithelial Cells via the Receptor–mediated Endocytosis Pathway".
J. Cell. Biochem., Suppl. O, (18 Part A), Abstract No. DZ 136 1994, p. 231, J. Yovandick et al: "Lactoferrin–mediated gene transfer: use of a nonantigenic, DNA–binding protein for receptor targeted gene therapy" & Keystone Symposium on gene therapy, Copper Mountain, Colorad, USA, Jan. 15–22, 1994.
Orkin et al. "Report and Recommendation of the Panel to Assess the NIH Investment in Research on Gene Therapy," NIH Report and Recommendation, Dec. 7, 1995.*
Jaenicke (1987) Folding and association of proteins. Prog. Biophysics Mol. Biol. 49:117–237, 1987.*
Braselmann et al. "A Selective transcriptional induction system for mammalian cells based on Gal4–estrogen receptor fusion proteins," Proc. Natl. Acad. Sci., vol. 90: 1657–1661, Mar. 1993.*
Nagaya et al. "Thyroid Hormone Receptor Mutants That Cause Resistance to Thyroid Hormone," J. of Biol. Chem., vol. 267: 13014–13019, Jun. 1992.*
Uhlen et al. "Gene Fusions for Purpose of Expression: An Introduction," Methods in Enzymology, vol. 185: 129–143, 1990.*

\* cited by examiner

Primary Examiner—Robert A. Schwartzman
(74) Attorney, Agent, or Firm—Lyon & Lyon LLP

(57) ABSTRACT

A complex for gene transfer a DNA molecule specifically and non-specifically bound to DNA binding protein. Additionally, it can include a chimeric compound for gene transfer. The chimeric compound has a DNA-binding element and a ligand binding element. The chimeric recombinant DNA can also include a binding protein which has a first element for binding to a receptor, a second element for binding to DNA, a third element for destabilizing endosomes and a fourth element for directing the traffic in a protein containing complex in the nucleus of a cell. The complex will be used for the treatment of a variety of diseases.

51 Claims, 10 Drawing Sheets

DNA-BINDING LIGANDS AS CARRIERS FOR DNA MEDIATED GENE TRANSFER

Previous scheme
Transferrin, insulin, asialo-orosomucoid

Proposed scheme
lactoferrin, recombinant chimeric proteins

ASIALO-LACTOFERRIN MEDIATED GENE TRANSFER INTO hepG2 CELLS

NATURAL OR RECOMBINANT DNA BINDING PROTEINS AS CARRIERS FOR GENE TRANSFER OR GENE THERAPY

This application is a continuation of application Ser. No. 08/054,493, filed Apr. 27, 1993 abandoned.

FIELD OF THE INVENTION

The present invention relates generally to the use of DNA binding proteins to effect or enhance entry of DNA into cells for gene transfer or gene therapy. It more particularly relates to the production of chimeric, recombinant, or synthetic proteins containing DNA binding elements for the purposes of effecting or enhancing gene transfer or gene therapy. It also relates to the use of lactoferrin for enhancing entry of DNA into cells.

BACKGROUND OF INVENTION

The essential process of somatic gene therapy is the ability to perform gene transfer. In this process, recombinant genes are introduced into selected somatic cells. In its simplest form, gene transfer can be performed by simply injecting minute amounts of DNA into the nucleus of a cell. This process is called microinjection (1). Once recombinant genes are introduced into a cell, they can be recognized by the cells normal mechanisms for transcription, and a gene product will be expressed. The utility of microinjection for gene therapy is obviously limited by the number of cells which can be injected. Thus, more efficient methods have been developed for introducing DNA into larger numbers of cells. These methods include: transfection, where DNA is precipitated with $CaPO_4$ and taken into cells by pinocytosis (2); electroporation, where cells are exposed to large voltage pulses to introduce holes into the membrane (3); lipofection/liposome fusion, where DNA is packaged into lipophilic vesicles which fuse with a target cell (4); and particle bombardment using DNA bound to small projectiles (5). Another important method for introducing DNA into cells is to couple the DNA to chemically modified proteins. These modified proteins have the ability to bind DNA through a chemically attached synthetic polylysine peptide, and bind to specific receptors on target cells. After these complexes are taken up by a specific receptor mediated endocytosis, the genes encoded by the DNA can be expressed by the target cell. Experiments have been performed with transferrin/polylysine/DNA complexes (6–11) as well as with asialoglycoprotein/polylysine/DNA complexes (12–25). The covalently, chemically combined natural ligands are used: (1) to specifically targeted DNA to different tissues; (2) to provide more efficient uptake process. These methods are limited because they require in vitro modification of the ligands using chemical or enzymatic methods in order to create a compound capable of binding DNA.

An important advance in methods of gene transfer was the demonstration that adenovirus proteins are capable of destabilizing endosomes and enhancing the uptake of DNA into cells. The admixture of adenovirus to solutions containing DNA complexes, or the binding of DNA to adenoviral particles by polylysine covalently attached to the adenovirus using protein crosslinking agents substantially improves the uptake and expression of the recombinant gene (6). Further studies have also suggested that proteins purified from other pathogenic bacteria, viruses or parasites may have similar properties.

In vivo studies with asialo-orosomucoid/polylysine/DNA complexes have shown that it is possible to achieve short term expression (several days) of recombinant genes in organs such as the liver (12–15). For this expression to be useful, however, it will be necessary to administer the complex repetitively either to treat intermittent symptoms of disease, or to establish chronic, steady-state levels of the gene product. One problem with repetitive administration using the asialo-orosomucoid/polylysine/DNA complex method, however, is that this complex is highly antigenic and that anaphylaxis can result from repetitive administration. Significantly, antibodies are formed against both the covalently modified orosomucoid as well as polylysine. Presumably, the natural protein (orosomucoid) which is not normally antigenic, is rendered antigenic by the covalent addition of polylysine. (It is less likely that removal of sialic acid makes this protein antigenic since this is a normal intermediate in synthesis and degradation of the protein.)

The present invention describes an improved method for gene transfer which enables specific targeting of DNA, enhanced uptake in various cell types and endosomal destabilization without the need to produce and purify viral proteins and without the need for covalent, chemical or enzymatic modifications to couple the DNA to the ligand. The present invention thus provides a method for gene transfer which will be easier and safer than currently available methods.

LITERATURE CITED IN TEXT (1) Capecchi M R. High efficiency transformation by direct microinjection of DNA into cultured mammalian cells. Cell 22:479–88 (1980).

(2) Chen C. and Okayama H. High-efficiency transformation of mammalian cells by plasmid DNA. Mol. Cell Biol. 7:2745–52 (1987).

(3) Chu G., Hayakawa H. and Berg P. Electroporation for the efficient transfection of mammalian cells with DNA. Nucleic Acids Res. 15:1311–26 (1987).

(4) Felgner P L., Gadek T R., Holm M., et al. Lipofection: a highly efficient, lipid-mediated DNA-transfection procedure. Proc. Natl. Acad. Sci. USA. 84:7413–7 (1987).

(5) Yang N S., Burkholder J., Roberts B, Martinell B. and McCabe D. In vivo and in vitro gene transfer to mammalian somatic cells by particle bombardment. Proc. Natl. Acad. Sci. 87:9568–72 (1990).

(6) Curiel D T., Agarwal S., Romer M U., Wagner E., Cotten M., Birnstiel M L. and Boucher R C. Gene transfer to respiratory epithelial cells via the receptor-mediated endocytosis pathway. Am. J. Respir. Cell. Mol. Biol. 6:247–52 (1992).

(7) Wagner E., Cotten M., Mechtler K., Kirlappos H. and Birnstiel M L. DNA-binding transferrin conjugates as functional gene-delivery agents: synthesis by linkage of polylysine or ethidium homodimer to the transferrin carbohydrate moiety. Bioconjug-Chem. 2:226–31 (1991).

(8) Wagner E., Cotten M., Foisner R. and Birnstiel M L. Transferrin-polycation-DNA complexes: the effect of polycations on the structure of the complex and DNA delivery to cells. Proc. Natl. Acad. Sci. USA. 88:4255–9 (1991).

(9) Wagner E., Zenke M., Cotten M., Beug H. and Birnstiel M L. Transferrin-polycation conjugates as carriers for DNA uptake into cells. Proc. Natl. Acad. Sci. USA. 87:3410–4 (1990).

(10) Zenke M., Steinlein P., Wagner E., Cotten M., Beug H. Birnstiel M L. Receptor-mediated endocytosis of transferrin-polycation conjugates: an efficient way to introduce DNA into hematopoietic cells. Proc. Natl. Acad. Sci. USA. 87:3655–9 (1990).

(11) Cotten M. Langle-Rouault F., Kirlappos H., Wagner E., Mechtler K., Zenke M., Beug H. and Birnstiel M L. Transferrin-polycation-mediated introduction of DNA into human leukemic cells: stimulation by agents that affect the survival of transfected DNA or modulate transferrin receptor levels. Proc. Natl. Acad. Sci. USA. 87:4033–7 (1990).

(12) Wilson J M., Grossman M., Wu C H., Chowdhury N R., Wu G Y. and Chowdhury J R. Hepatocyte-directed gene transfer in vivo leads to transient improvement of hypercholesterolemia in low density lipoprotein receptor-deficient rabbits. J. Biol. Chem. 267:963–7 (1992).

(13) Wilson J M., Grossman M., Cabrera J A., Wu C H., Wu G Y. A novel mechanism for achieving transgene persistence in vivo after somatic gene transfer into hepatocytes. J. Biol. Chem. 267: 11483–9 (1992).

(14) Wu G Y., Wilson J M., Shalaby F., Grossman M., Shafritz D A. and Wu C H. Receptor-mediated gene delivery in vivo. Partial correction of genetic analbuminemia in Nagase rats. J. Biol. Chem. 266:14338–42 (1991).

(15) Wu C H., Wilson J M. and Wu G Y. Targeting genes: delivery and persistent expression of a foreign gene driven by mammalian regulatory elements in vivo. J. Biol. Chem. 264: 16985–7 (1989).

(16) Wu G Y. and Wu C H. Receptor-mediated in vitro gene transformation by a soluble DNA carrier system. J. Biol. Chem. 262:4429–32 (1987).

(17) Wu G Y. and Wu C H. Targeted delivery and expression of foreign genes in hepatocytes. Targeted Diagn. Ther. 4:127–49 (1991).

(18) Wu G Y. and Wu C H. Delivery systems for gene therapy. Biotherapy 3:87–95 (1991).

(19) Wu G Y. and Wu C H. Receptor-mediated gene delivery and expression in vivo. J. Biol. Chem. 263:14621–4 (1988).

(20) Wu G Y. and Wu C H. Evidence for targeted gene delivery to Hep G2 hepatoma cells in vitro. Biochemistry 27:887–92 (1988).

SUMMARY OF INVENTION

An object of the present invention is the use of natural DNA-binding proteins to enhance the entry of DNA into cells.

An additional object of the present invention is the use of natural DNA-binding proteins bound to DNA for the purposes of gene transfer and somatic gene therapy.

A further object of the present invention is the use of lactoferrin as a DNA-binding protein for the purposes of effecting or enhancing the entry of DNA into cells for the purposes of gene transfer or gene therapy.

Another object of the present invention is the use of recombinant DNA-binding proteins to enhance the entry of DNA into cells.

A further object of the present invention is the use of recombinant DNA-binding proteins bound to DNA for the purposes of gene transfer and somatic gene therapy.

An additional object of the present invention is the design of chimeric proteins containing elements that bind to DNA and elements which destabilize the endosome.

An additional object of the present invention is the design of chimeric proteins containing elements which effect the trafficking of the DNA or DNA-protein complex out of the endosome.

An additional object of the present invention is the design of chimeric proteins containing elements that bind to DNA and elements which direct the trafficking of the DNA or DNA-protein complex to the nucleus.

Thus in accomplishing the foregoing objects, there is provided in accordance with one aspect of the present invention a complex for gene transfer comprising a DNA molecule bound to a DNA-binding protein.

In one embodiment of the present invention the DNA-binding protein binds nonspecifically to single strand, double strand, circular, or supercoiled molecules comprised of deoxyribonucleic acid.

In an embodiment of the present invention the DNA-binding protein may bind specifically to particular nucleotide sequences incorporated within the DNA.

In an additional embodiment of the present invention, the DNA-binding protein is a chimeric protein containing an element that binds to DNA and a ligand element which binds to specific receptors on target cells.

In one embodiment of this invention, lactoferrin constitutes both the DNA-binding elements and the ligand elements.

In specific embodiments of this invention, the DNA-binding element is derived from the set of genes encoding proteins including lactoferrin, histones, steroid hormone receptors, trans acting regulatory elements, basic nuclear proteins, or chromatin elements; and the ligand element is derived from the set of genes encoding proteins including protein hormones, glycoprotein hormones, serum proteins, vitamin binding proteins, transcobalamin I, transcobalmin II, R binder, intrinsic factor, cell surface proteins, cytokines, interleukins, interferons, neurotropic peptides, viral proteins, bacterial proteins or cell adhesion molecules.

In another embodiment of this invention, an additional element which effects trafficking out of the endosome is used. This element is derived from the set of genes encoding proteins including elements of adenovirus, parainfluenza virus, proteins from viruses, proteins from parasites, and proteins from bacteria.

In a specific embodiment of this invention, an element which fuses to cell membranes including the hemagglutinin of sendai virus and influenza virus are used.

Another embodiment of the present invention includes an element which directs trafficking of proteins or protein complexes to the nucleus. This element is derived from the set of gene encoding proteins including nuclear proteins from mammals, nuclear hormone receptors, viral proteins, non-viral proteins.

In an additional embodiment of this invention the DNA-binding protein is a riboprotein. The riboprotein can bind to the DNA by hybridization or by triplex formation between the ribonucleotide sequence on the riboprotein and the DNA.

One specific embodiment of the present invention comprises a chimeric recombinant DNA-binding protein. The DNA-binding protein is comprised of elements derived from the set including: a first element for binding to a receptor on the target cell, a second element for binding to DNA, a third element capable of effecting trafficking out of the endosome or fusing with membranes, and a fourth element capable of directing trafficking of proteins or protein containing complexes to the nucleus of the cell. These elements are combined in tandem fashion to comprise a single protein molecule. These elements are combined in an order, spacing, and orientation appropriate for their multiple and specific functions.

Other and further objects, features and advantages will be apparent from the following descriptions of the presently preferred embodiments in the invention which are given for

BRIEF DESCRIPTION OF THE DRAWINGS

Figure Legends

The drawings are not necessarily to scale. Certain features of the invention may be exaggerated in scale or shown in schematic form in the interest of clarity and conciseness.

DETAILED DESCRIPTION OF THE INVENTION

It will be readily apparent to one skilled in the art that various substitutions and modification may be made to the invention disclosed herein without departing from the scope and spirit of the invention.

Definitions

As used herein, "Natural DNA-binding protein" means a protein whose natural sequence is capable of binding nonspecifically to DNA or specifically to certain nucleic acid sequences found within natural or recombinant DNA molecules. Natural DNA-binding proteins may be purified from natural sources. Alternatively, natural DNA-binding proteins may be produced by recombining the gene for the natural DNA-binding protein in an expression vector capable of directing expression of the DNA-binding protein in an appropriate host cell. The protein can then be produced in a variety of cells including mammalian cells, non-mammalian cells, insect cells, bacterial cells, yeast cells, fungal cells, or transgenic animals. It will be apparent to one skilled in the art that proteins produced in these organisms may have specific post-translational modifications but will retain their natural protein sequence.

As used herein "Recombinant DNA-binding protein" means a protein whose natural sequence has been altered using recombinant DNA methods. Alterations may include eliminating segments of the natural sequence, attenuating the length of the natural sequence at the carboxyl or amino terminal ends, changing specific amino acids present in the natural sequence by altering codons encoding the protein, adding additional amino acids to the natural sequence, or creating chimeric proteins comprised of segments from several different natural or recombinant proteins. The recombinant DNA-binding proteins are created using recombinant DNA, cloning, or amplification methods. In these procedures, genetic sequences are constructed which encode the desired DNA-binding protein with a genetic element which will direct expression of the recombinant protein in a desired host. The recombinant proteins can be produced in a variety of hosts including mammalian cells, non-mammalian cells, insect cells, bacterial cells, yeast cells, fungal cells, or transgenic animals.

As used herein a "DNA-binding element" can be DNA-binding protein, a recombinant DNA-binding protein, chimeric proteins or other natural molecules whose sequence is capable of binding nonspecific DNA specifically to certain nucleic acid sequences found within natural or recombinant DNA molecules.

As used herein "Chimeric proteins" means proteins containing sequences from two or more different natural or recombinant proteins. Chimeric proteins are produced using recombinant DNA methods.

Figure 1:
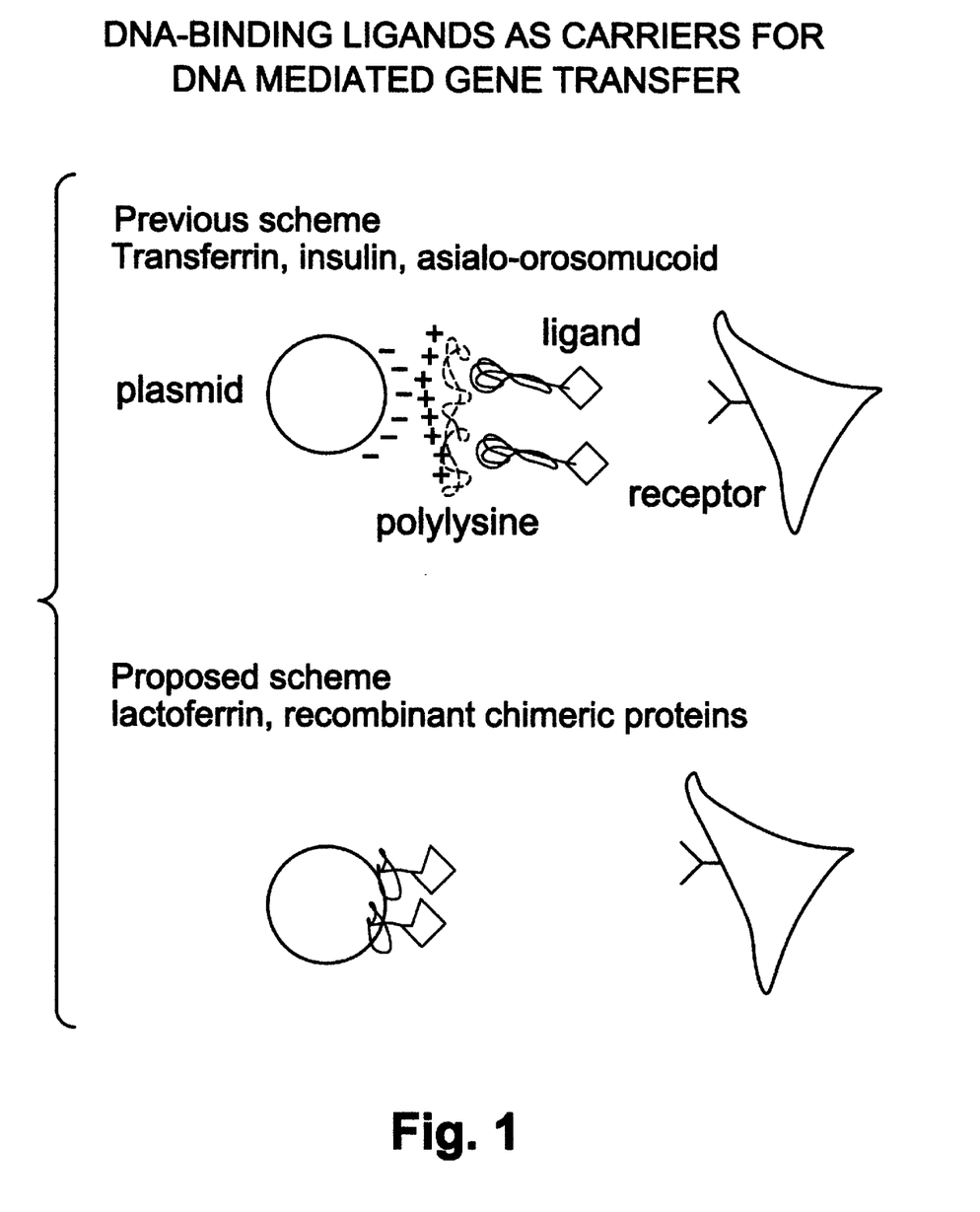
FIG. 1 compares the previous schemes for gene therapy with the scheme of the present invention. The previous schemes for gene therapy required covalent modification of a ligand by coupling the ligand to polylysine. A complex could then be formed with the negative charge of DNA binding to the positive charge of polylysine. The present scheme describes the use of proteins with DNA-binding activity, thus obviating any requirement for covalent modification of a ligand for use in gene transfer.
Figure 2:
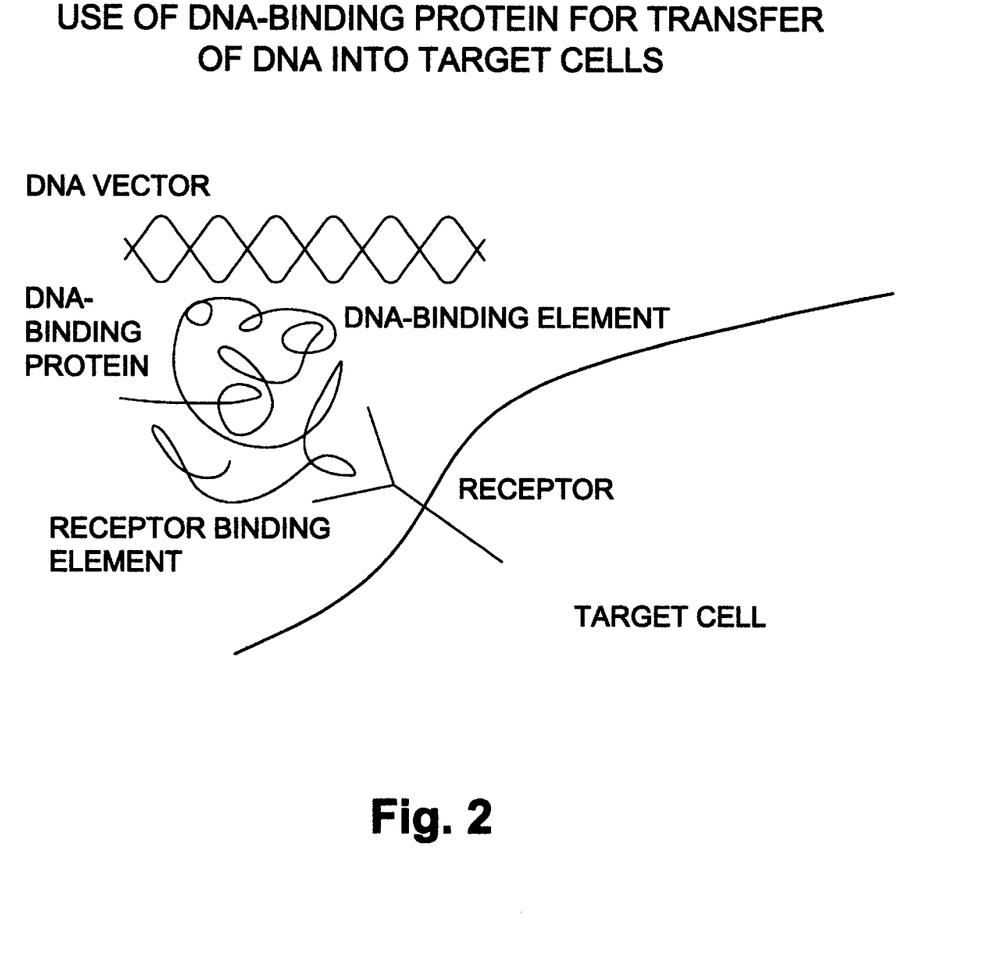
FIG. 2 shows a schematic of the use of a DNA-binding protein for transfer of DNA into target cells.
Figure 3:
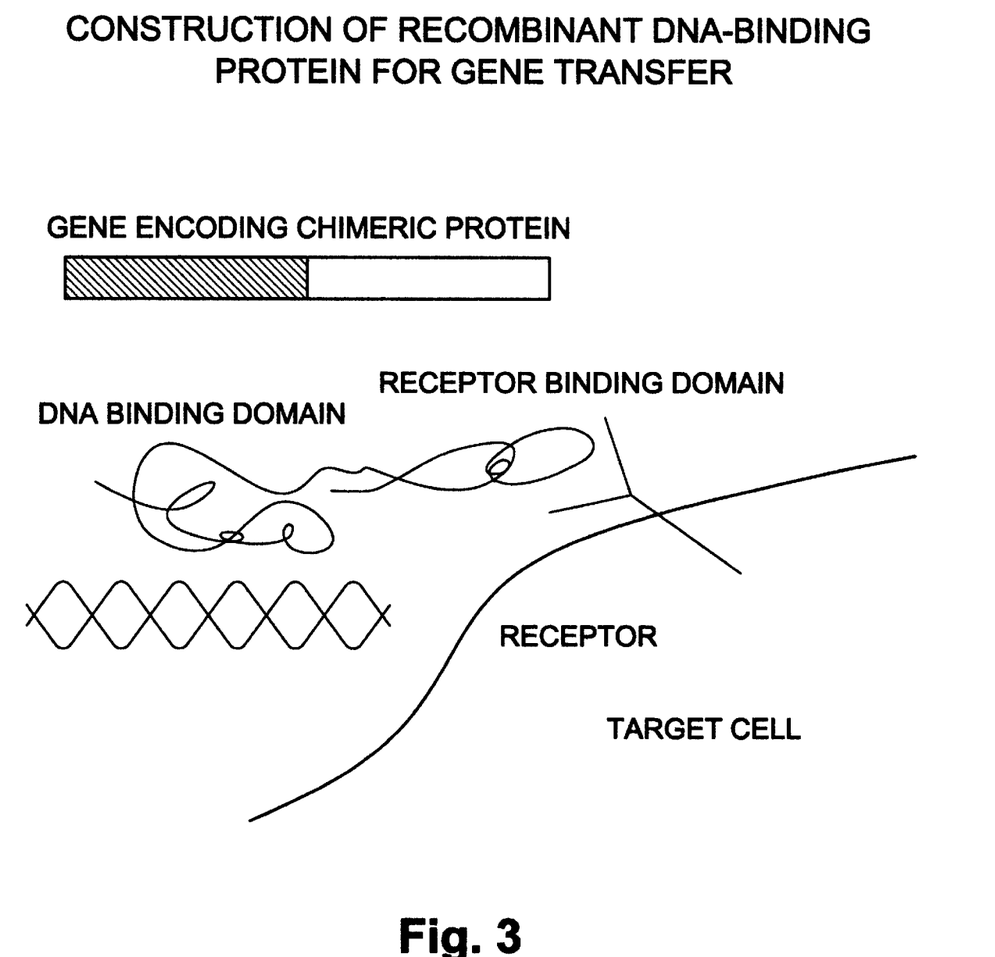
FIG. 3 shows the construction of recombinant DNA-binding protein for gene transfer.

A recombinant gene can be assembled which encodes a chimeric protein that has both a DNA-binding domain and a receptor binding domain. A complex containing this chimeric protein will bind both the DNA vector and the receptor on the target cell leading to uptake and expression of the recombinant Gene (see FIG. 3).

Figure 4:
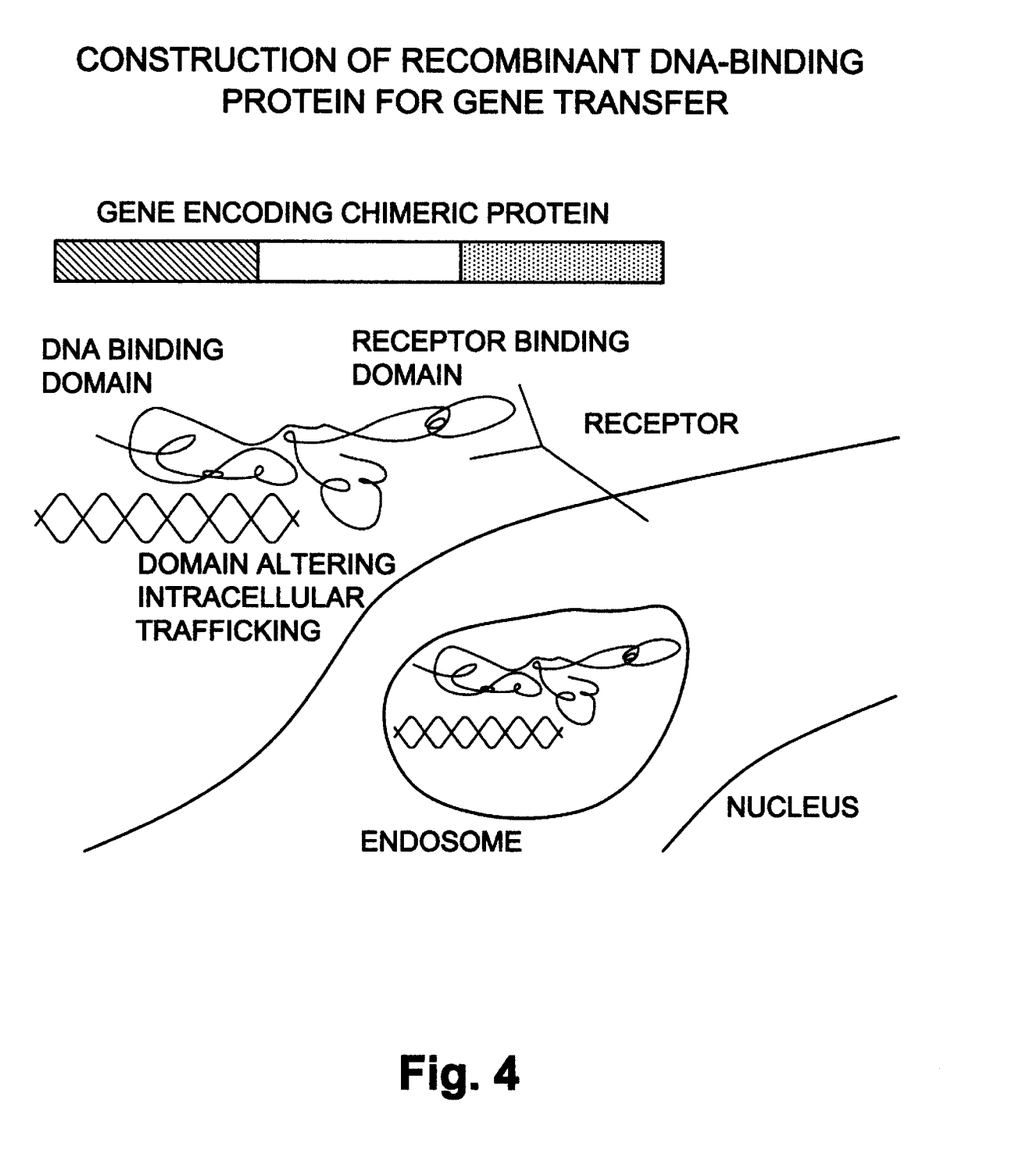
FIG. 4 shows an alternative construction of recombinant-DNA-binding protein for gene transfer.

Further, a recombinant gene can be assembled which encodes a chimeric protein that has a DNA-binding domain, a receptor binding domain, and a domain capable of altering intracellular trafficking of the complex (i.e. exit from the endosome or entry into the nucleus. A complex containing this chimeric protein will bind both to the DNA vector and the receptor on the target cell leading to uptake of DNA into the cell. Once within the cell the trafficking of the complex is enhanced by the presence of a domain which alters the rate of exit from the endosome or entry into the nucleus (see FIG. 4).

As used herein "Recombinant DNA methods" includes the process of separating fragments of DNA, joining fragments of DNA, synthesizing fragments of DNA, or copying fragments of DNA or RNA, amplifying fragments of DNA, or any other manipulations of DNA or RNA undertaken for the purposes of producing a protein capable of binding DNA and effecting or enhancing gene transfer or gene therapy. This may involve the use of chemical modifications or enzymes including restriction endonuclease, exonuclease, endonuclease, ligase, DNA polymerase, methylase, demethylase or RNA polymerase. It should be emphasized that these modifications take place at the level of DNA rather than protein. The present invention is thus fundamentally different from the methods of the prior art.

As used herein Vector means a DNA molecule comprised of single strand, double strand, circular, or supercoiled DNA. The vector is comprised of the following elements linked sequentially at appropriate distances for allowing functional gene expression: a promotor, a 5' mRNA leader sequence, a transcription initiation site, a nucleic acid cassette, a 3' untranslated region, and a polyadenylation site. One or more of these elements can be eliminated for specific applications. The nucleic acid cassette can include a restriction site for insertion of the nucleic acid sequence to be expressed. In a functional vector the nucleic acid cassette contains the nucleic acid sequence to be expressed including translation initiation and termination sites, As used herein "Ligand" means a natural or recombinant protein capable of binding to a specific or nonspecific receptor associated with a target cell.

As used herein "Carrier" means a molecule bound to DNA which effects or enhances the process of gene transfer.

As used herein "DNA-protein complexes" means the complex formed between a DNA molecule or vector and a natural or recombinant DNA-binding protein.

As used herein "Gene transfer" means the process of introducing a foreign DNA molecule into a cell. Gene transfer is commonly performed for the purposes of expressing a particular product encoded by the gene. The product may include a protein, polypeptide, anti-sense DNA or RNA, or enzymatically active RNA. Gene transfer can be performed in cultured cells or by direct administration into animals. Generally gene transfer involves the process of DNA contact with a target cell by non-specific or receptor mediated interactions, uptake of DNA into the cell through the membrane or by endocytosis, and release of DNA into the cytoplasm from the plasma membrane or endosome. Expression may require, in addition, movement of the DNA into the nucleus of the cell and binding to appropriate nuclear factors for transcription.

As used herein "Gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the DNA or DNA-protein complex into the patient.

As used herein, "cytokine" refers to a protein or glycoprotein which acts on cells of the immune system to regulate the immune response.

As used herein, "neuropeptide" refers to a protein or glycoprotein which acts on cells of the central or peripheral nervous system to regulate neurological development or activity.

As used herein, "receptor" refers to a molecule within a cell that interacts with an exogenously applied substance and mediates an effect of that substance on the cell.

The present invention describes an improved method for gene transfer. A specific embodiment is a complex for gene transfer comprising a DNA molecule specifically or non-specifically bound to a DNA-binding protein. The DNA-binding protein may be selected from naturally occurring proteins or the DNA-binding protein can be produced by recombinant methods which create a new, chimeric protein or protein with an altered amino acid sequence.

One skilled in the art readily recognizes that by identifying or constructing a protein which is autonomously capable of binding DNA, a DNA-protein complex can be assembled without further chemical or enzymatic modifications. If this DNA-binding protein has, in addition, elements which may effect or enhance the process of gene transfer, then this DNA-binding protein may be used to effect or enhance the process of gene transfer or gene therapy. This is without the need for chemical covalent or enzymatic modifications of the protein and provide significant advantage in manufacturing and quality control.

Another embodiment of the present invention is a chimeric recombinant DNA-binding protein comprising a first element for binding to a receptor on a target cell and a second element required for binding to DNA. Further enhancements can include a third element capable of directing the trafficking of DNA out of the endosome; and/or a fourth element capable of directing the traffic in a protein or protein complex to the nucleus of a cell. The various combination of the above four elements are combined to comprise a single protein molecule and the order, space and orientation of the elements is appropriate for the multiple and specific functions of the molecule. These chimeric proteins are designed to contain elements capable of effecting several different processes required for gene transfer. The specific element can be selected from: (1) ligands for specific or nonspecific receptors on the surface of a cell, thus bringing DNA into contact with the cell; (2) fusion of the DNA-protein complex with the cell membrane; (3) endocytosis of the DNA-protein complex, destabilization of the endosome leading to release of the DNA-protein complex into the cell; and (4) trafficking of the DNA-protein complex to the nucleus.

The chimeric protein is constructed by recombining gene sequences which encode the desired elements into a single DNA molecule and expressing the product of the recombinant gene in an appropriate host.

In the chimeric protein these elements are positioned in a single linear sequence with the elements positioned in an order, spacing, and orientation that is appropriate for the desired activity.

Any one of the DNA-binding elements can bind nonspecifically to different forms of DNA including single strand, double strand, linear, circular, or supercoiled or may bind specifically to particular sequences within the sequence. In this embodiment, the bond between the DNA-binding protein and DNA will be non-covalent.

The elements which are ligands for specific or nonspecific receptors are selected based on their ability to bind to the desired target cell with appropriate affinity. This binding will bring the DNA-protein complex into contact with the cell which is the first step in gene transfer. These elements can be selected from the set including proteins, hormones, glycoprotein hormones, serum proteins, secreted proteins, cell surface proteins, cytokines, interleukins, interferons, neurotropic peptides, viral proteins, or bacterial proteins, cell adhesion molecules, immunoglobulins, T-cell receptors, cell surface markers from mature or immature bone marrow elements, or cell surface markers from lymphocytes.

In the present invention a DNA-binding protein containing both a DNA-binding element and a receptor binding element (ligand) is used for gene transfer into target cells. A complex containing the DNA-binding protein and the DNA vector will bind to receptors on the target cell leading to uptake and expression of the recombinant gene. In the preferred embodiment of this invention the DNA-binding protein is lactoferrin.

One skilled in the art will recognize that it is possible to select the ligand element to direct gene transfer or gene therapy to different cell types. For example, IL2 for T-cells; somotostatin for pancreatic B-cells; endorphin for regions of the brain, and MSH for melanocytes.

Elements which cause fusion of the DNA-protein complex with the cell membrane will cause the DNA bound to this complex to be introduced into the cytoplasm of the cell. These elements can be selected from the set including the hemagglutinin of sendai virus, parainfluenza virus, and HIV.

The elements causing endocytosis of the DNA-protein complex are related to the elements which are ligands for various receptors in that the interaction of some ligands with their receptor is the stimulus for endocytosis. Thus the selection of the ligand will determine whether the DNA-protein complex is taken up by endocytosis into the targeted cell.

One skilled in the art will recognize that by incorporating elements capable of fusing with the cell membrane or elements capable of causing endocytosis, the method by which DNA is taken up by the cell can be selected. The efficiency of this gene transfer process can be enhanced by optimizing the structure of the chimeric DNA-binding protein.

The elements that effect trafficking of materials out of the endosome or cause destabilization of the endosome leading to release of the DNA-protein complex are derived from viral, bacterial or parasitic proteins for which endosomal destabilization is known to be an essential part of the viral life cycle. This well-known property of adenovirus or other viruses prevents the viral particle from being destroyed during the process of infection. It has been shown that the presence of adenoviral particles during the process of receptor mediated endocytosis greatly enhances the efficiency of uptake of intact DNA. The construction of chimeric proteins containing specific genetic elements known to cause endosomal destabilization enhances the process of gene transfer.

The elements directing trafficking of the DNA-protein complex to the nucleus of the cell are derived from proteins which are normally synthesized on cytoplasmic ribosomes and then directed to the nucleus by specific sequences within the protein. These elements have been described on many proteins and have been shown to direct the trafficking of recombinant proteins to the nucleus. These elements can be derived from the set including nuclear proteins from mammals, nuclear hormone receptors, viral proteins and non-viral proteins.

One skilled in the art will recognize that transcription or replication of DNA occurs in the nucleus. Thus the presence of a nuclear localizing sequence enhances the efficiency of gene expression after the process of gene transfer.

The natural or recombinant DNA-binding protein may undergo post-translational modifications after synthesis on cytoplasmic ribosomes. Thus the protein may be a riboprotein, glycoprotein, phosphoprotein, or lipoprotein. One skilled in the art will recognize that recombinant proteins expressed in different cell types can undergo different post-translational modifications. Thus expression of a natural DNA-binding protein in different cells can produce a product which has the natural protein sequence but different post-translational modifications. For example, expression of a glycoprotein in a cell which is incapable of adding sialic acid to the carbohydrate will produce an asialoglycoprotein.

Proteins with different post-translational modifications can have properties which are beneficial for gene transfer or gene therapy. For example, asialoglycoproteins will bind to a specific receptor on hepatic cells and DNA-asialoglycoprotein complexes have been shown to be taken up after this interaction. Thus DNA-binding glycoproteins produced in a sialotransferase deficient cell are useful to target gene delivery to the liver without further chemical or enzymatic modifications.

Complexes between natural or recombinant DNA-binding proteins can be administered by any conventional parenteral route including intravenous administration, injection directly into organs or somatic structures, intramuscular injection, intradermal injection, subcutaneous injection, topical administration and oral administration.

The use of lactoferrin as a DNA-binding protein provides a method of oral gene therapy. Lactoferrin is relatively resistant to acid hydrolysis in the stomach as well as the action of digestive enzymes and bases in the intestines. Lactoferrin is also protected from degradation in the stomach and small intestines by being incorporated into lipid micelle within milk (the cream layer). The admixture of elements of milk to DNA-lactoferrin complexes can protect the DNA-protein complex from degradation. Complexes entering the small bowel bind to the lactoferrin receptor on these cells leading to efficient gene transfer.

The following examples are offered by way of illustration and are not intended to limit the invention in any manner.

EXAMPLE 1

Formation of Lactoferrin-DNA Complexes for Gene Transfer

Figure 5:
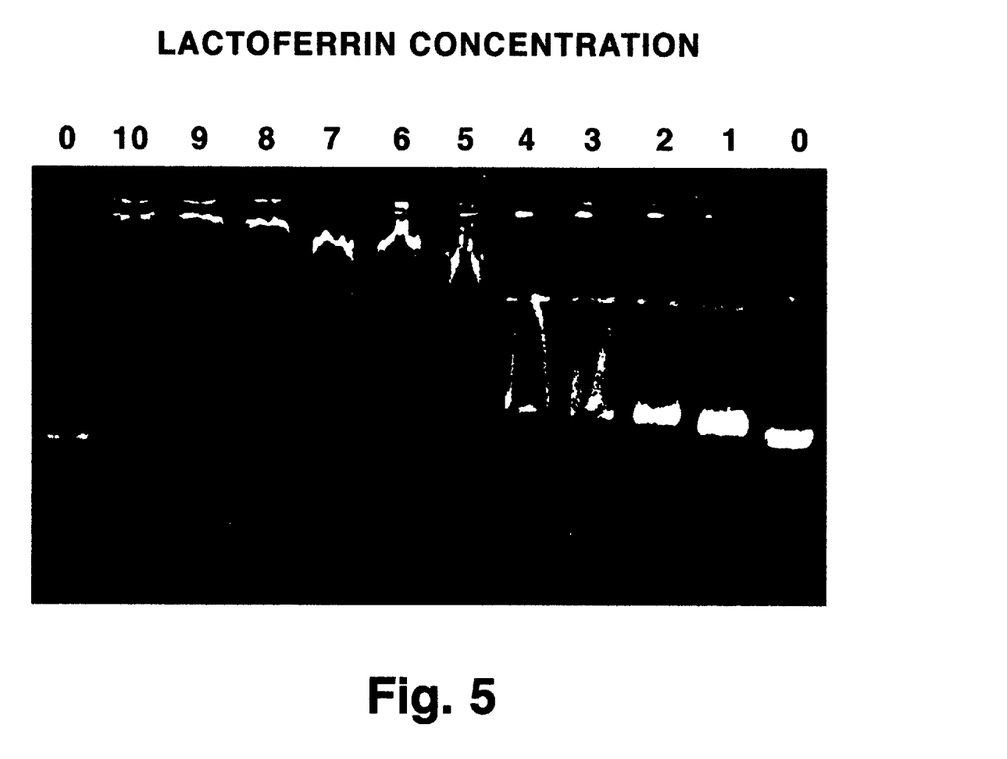
FIG. 5 shows binding of lactoferrin to plasmid DNA.
Figure 6:
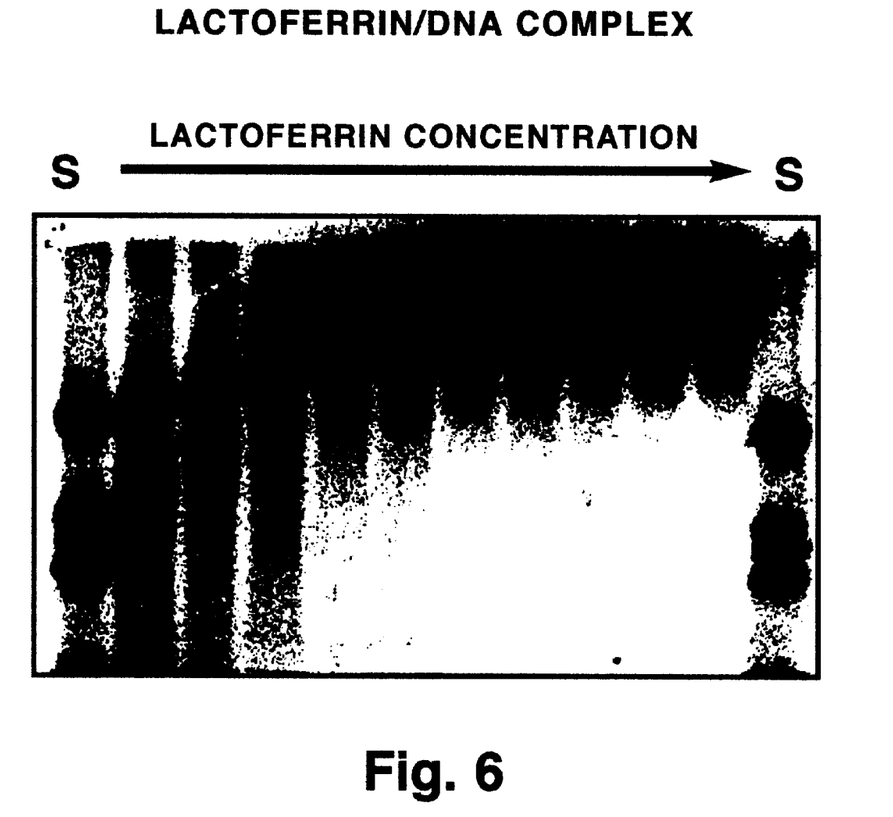
FIG. 6 shows binding of lactoferrin to linear DNA.
Figure 7:
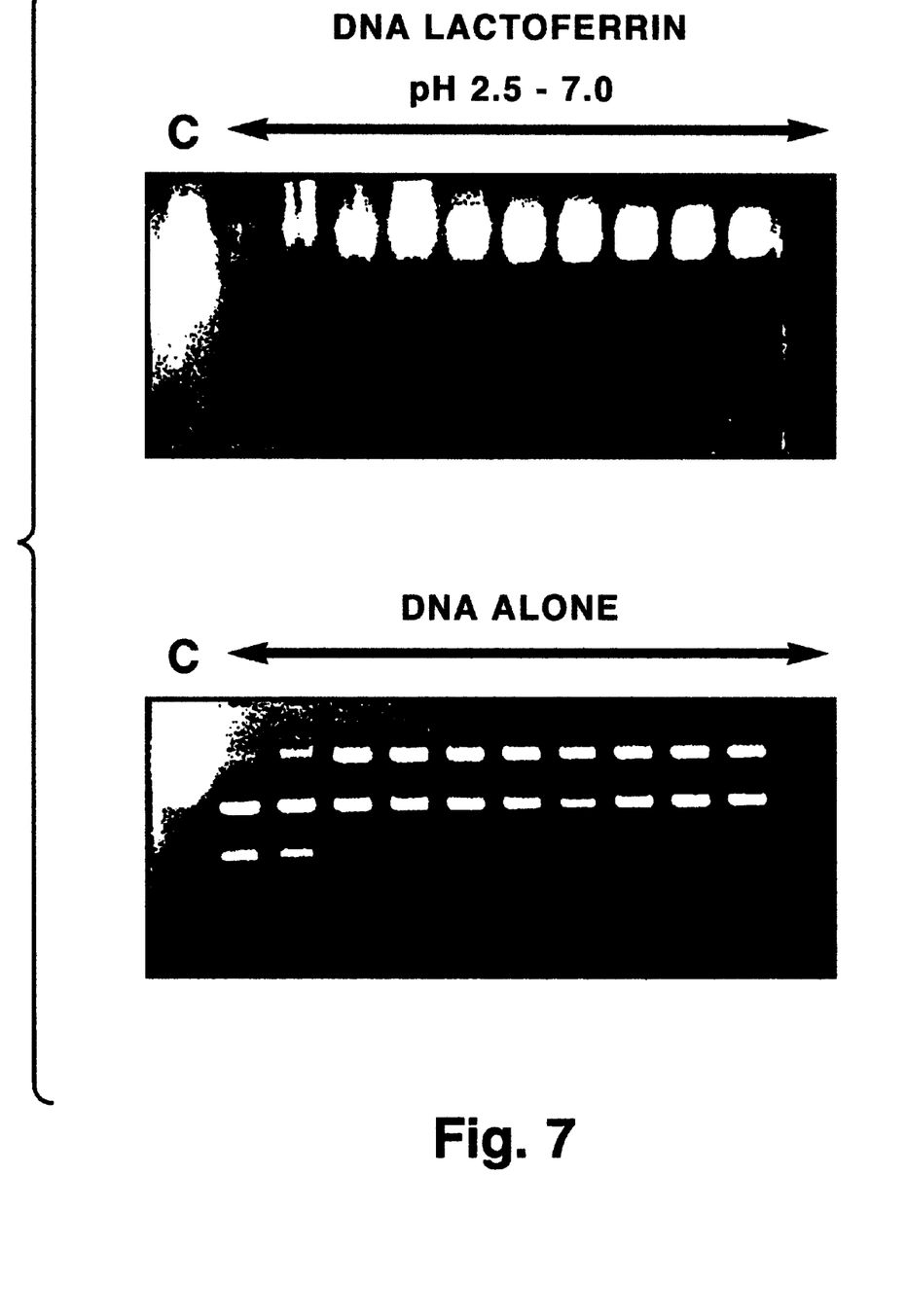
FIG. 7 shows protection of DNA from acid hydrolysis by lactoferrin.

Lactoferrin will bind linear, circular, or supercoiled DNA in solution and form a complex which can be assayed by a gel retardation assay in which the migration of DNA decreases as the size of the protein/DNA complex increases (FIG. 5–6). Several different forms of this complex are apparent on gel retardation assays depending upon the stoichiometry of association between the DNA and lactoferrin molecules. At low concentrations of lactoferrin there is a minimal retardation of DNA migration in the gel suggesting that the complex contains few copies of lactoferrin. At high concentrations of lactoferrin the complex does not enter the gel suggesting that a larger complex, containing many copies of lactoferrin, has been formed. The complex is stable over a wide range of salt concentrations (0–1 mM) salt, and pH (pH 2–12) (FIG. 7). Of particular significance is the fact that at low pH, DNA is apparently protected from hydrolysis while it is part of the DNA complex (FIG. 7).

DNA is incubated with lactoferrin at different concentrations and then run an agarose gel. The formation of a lactoferrin-DNA complex is monitored by the retardation of DNA migration into the gel. With higher concentrations of lactoferrin there is progressive retardation of DNA migration indicating that the size and composition of the particle can be specifically altered (see FIG. 5).

DNA is incubated with lactoferrin after digestion with a restriction enzyme to produce linear fragments and end labeled with [$^{32}$P]-dCTP to allow visualization after gel electrophoresis. The formation of lactoferrin-DNA complex is monitored by the retardation of DNA migration into the gel. With higher concentrations of lactoferrin there is progressive retardation of DNA migration indicating that the size and composition of the particles can be specifically altered (see FIG. 6).

Complexes of DNA and lactoferrin were incubated in buffers at different pH between 2.5 and 7.0 (top). Control experiments were performed under identical conditions without lactoferrin (bottom). Hydrolysis of the DNA is evident by the appearance of lower bands representing linear (broken) DNA at pH 2.5 and pH 3.0 in the lower panel. In contrast the lactoferrin DNA complex remains intact (see FIG. 7).

EXAMPLE 2

Lactoferrin-DNA Complexes for Oral Gene Therapy

Lactoferrin is normally absorbed from the gut via the epithelial cells. It is normally protected from degradation in the stomach and small intestines by its resistance to acid and protease as well as by forming a complex with lipid micelles in the cream layer of milk. There are several pathways by which lactoferrin may be taken up after oral administration. It may be taken up by receptor mediated endocytosis into the endosome, or it may pass through the intestinal barrier by a transcytotic pathway and enter the general circulation.

For oral gene therapy the lactoferrin DNA-complex is administered orally by itself or in a formulation containing lipids derived from, or similar to, those in the cream layer of milk. DNA bound to the lactoferrin complex is protected from degradation in the stomach and proximal small bowel and pass through the small bowel without dissociation. The complexes reaching the small bowel bind to the lactoferrin receptor in the cells lining the bowel and enter the cells by receptor mediated endocytosis.

EXAMPLE 3

Parenteral Therapy with Lactoferrin DNA Complexes

Many cell types have receptors for lactoferrin. Parenteral (intravenous) administration of the lactoferrin-DNA complex leads to uptake of this complex in a variety of cell types that have the lactoferrin receptor and are in contact with the vascular space. This provides a relatively non-specific means for introducing DNA into a variety of cells in vivo. Tissue specific gene expression is attained by employing vectors with tissue-specific promoters such that the therapeutic gene is only expressed in cells permissive to that promoter and not other cells which have the lactoferrin receptor.

EXAMPLE 4

Inhalation Therapy with Lactoferrin-DNA Complexes

Lactoferrin-DNA complexes can be administered by inhalation with use of a nebulizer of direct instillation through an endotracheal tube. This complex will bind to receptors on epithelial cells or alveolar cells lining the airways and enhance the efficiency of gene transfer. Large complexes may be endocytosed specifically by alveolar macrophages enabling efficient gene transfer to these cells.

EXAMPLE 5

Hepatic Gene Transfer with Asialolactoferrin

Liver cells contain a highly specific, high affinity receptor for asialoglycoproteins. By exposing a liver cell to the complex comprised of asialolactoferrin and DNA, this complex will bind to the asialoglycoprotein receptor and be taken into the cell by the process of receptor mediated endocytosis.

Lactoferrin is a glycoprotein which normally contains carbohydrate elements containing terminal sialic acid. Asialolactoferrin may be constructed using several methods. One involves treating native lactoferrin with the enzyme sialidase to remove terminal sialic acids. The other is to introduce a recombinant cDNA clone for lactoferrin into a CHO cell line deficient in the enzyme required for adding sialic acid to glycoproteins (sialotransferase), or other eukaryotic or prokaryotic hosts similarly lacking this enzymatic function. Such hosts will produce asialo-lactoferrin which requires no subsequent modification. This molecule has been shown to exhibit DNA-binding properties indistinguishable from native lactoferrin.

Asialo-lactoferrin has been shown to effect gene transfer in cultured hepatoma cells (hepG2) with efficiencies equal to, or greater than, native lactoferrin-DNA complexes or other methods requiring covalent coupling and modification of proteins such as orosomucoid. These coupled and covalently modified compounds have been shown to be effective vehicles for gene transfer into the liver in cell culture and experimental animals. The in vitro experiments indicate that asialolactoferrin-DNA complexes provide a similar method for gene delivery without the need for enzymatic or chemical modifications and less potential for antigenicity.

EXAMPLE 6

Hepatic Gene Transfer Based on Particle Size

The size of the complex formed between lactoferrin and DNA can be varied by the ratio of lactoferrin: DNA (FIG. 6–7), by the addition of iron, or other means. Complexes which are injected intravenously that are too large to exit from the endothelium, but are small enough to exit the sinusoid of the liver and be preferentially endocytosed by hepatic cells would be suitable for hepatic gene transfer.

EXAMPLE 7

Enhanced Hepatic Gene Transfer Using Recombinant Asialolactoferrin

The specificity of hepatic gene transfer using asialolactoferrin via the asialoglycoprotein receptor may be compromised by the ability of the asialolactoferrin to bind to lactoferrin receptors on other tissues. Site specific mutagenesis is employed to disrupt the receptor binding determinants of lactoferrin while retaining the sites at which the carbohydrate is attached. The asialo-form of the mutagenized, recombinant gene product provides enhanced hepatic gene transfer since it would be less likely to bind to other sites.

EXAMPLE 8

Use of Recombinant, Chimeric DNA-Binding Proteins for Gene Therapy

A DNA-protein complex with altered tropism is constructed by recombining genetic elements encoding a DNA-binding protein with genetic elements encoding the binding determinants of a natural ligand. These elements are combined in an order, spacing, and orientation so that the ligand elements which bind to the receptor are exposed in the DNA-protein complex.

For example, a gene fragment encoding the 5' end of the cDNA encoding lactoferrin encodes the amino terminal portion of lactoferrin where the DNA-binding determinants reside. A recombinant gene can be constructed with this genetic element and the sequences encoding IL-2 attached at the 3' end of the sequence and encoding the carboxyl terminal portion of the protein. The gene product encoded by this chimeric clone can be produced in prokaryotic or eukayotic expression systems. The resulting gene product will bind DNA through the DNA-binding determinants from lactoferrin and will be capable of binding to the IL-2 receptor on T-cells and many T-cell malignancies. This complex may thus be used to introduce genes into T-cells to alter the function of the immune system, eliminate cells with the HIV provirus, or kill cells arising from T-cell malignancies.

EXAMPLE 9

Chimeric Proteins for Enhanced Gene Transfer

A DNA-protein complex capable of enhanced gene transfer may be constructed by recombining genetic elements encoding a DNA-binding protein with genetic elements encoding a hemagglutinin, for example, the fusogenic peptide from para-influenza virus. These DNA elements are combined in an order, spacing, and orientation so that the chimeric protein retains the DNA-binding and receptor binding determinants. The chimeric clone is introduced into eukaryotic or prokaryotic cells to produce the recombinant gene product.

The fusogenic peptide from para-influenza virus effects fusion with periplasmic membranes or endosomes. Thus the complex containing the chimeric protein with the fusogenic peptide fuses with membranes after binding to target cells, and thus bypasses endosomal uptake, or may have enhanced uptake from the endosome after endocytosis. This increases the efficiency of gene transfer.

EXAMPLE 10

Chimeric DNA-Binding Proteins with Tropism for Specific Receptors (2)

A gene fragment encoding the DNA-binding sequences from lactoferrin is recombined with a gene fragment encoding the receptor binding sequences of IL-2. This complex binds to DNA through the DNA-binding domain of lactoferrin and binds to mammary cells expressing the IL-2 receptor. The use of this chimeric protein enables gene delivery to T-cells and various leukemic cells. This is useful in the regulation of T-cell function and in treatment of T-cell malignancies.

EXAMPLE 11

Lactoferrin Mediated Transfer Into HepG2 (Hepatoma) Cells

Figure 8:
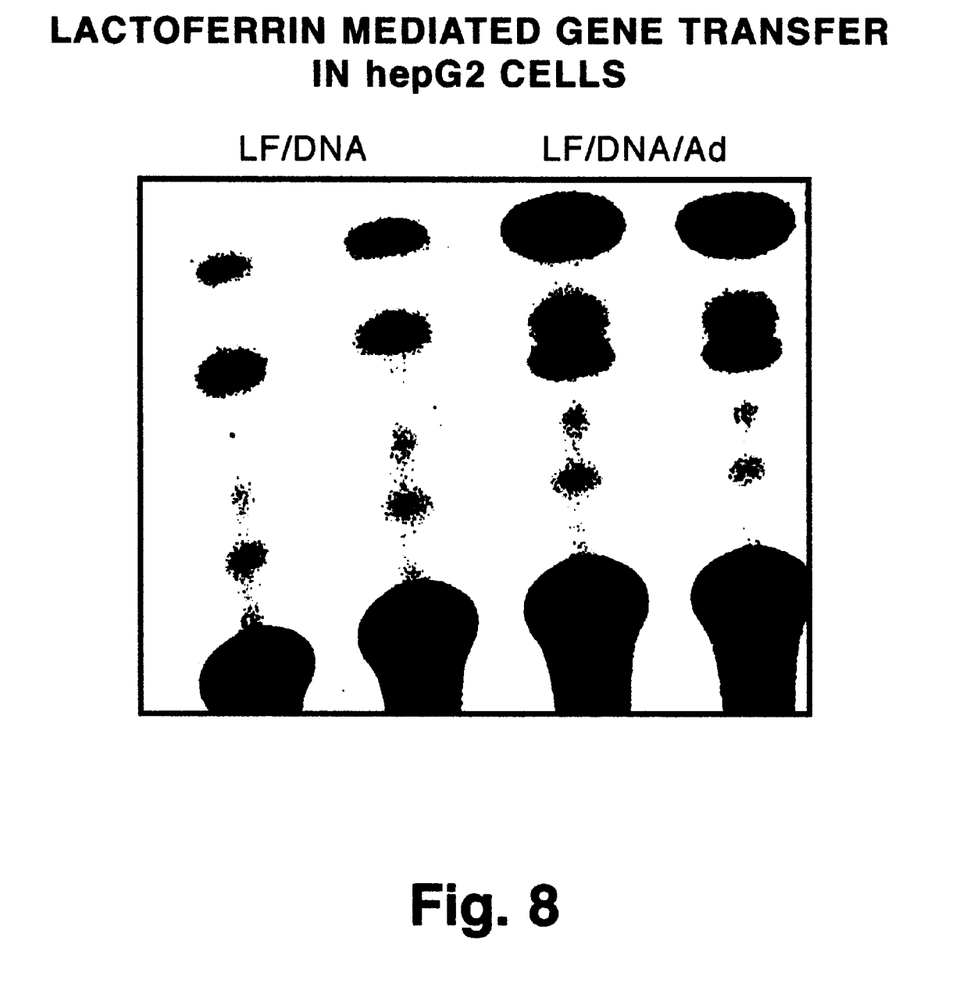
FIG. 8 shows lactoferrin mediated gene transfer into hepG2 (hepatoma) cells.
Figure 9:
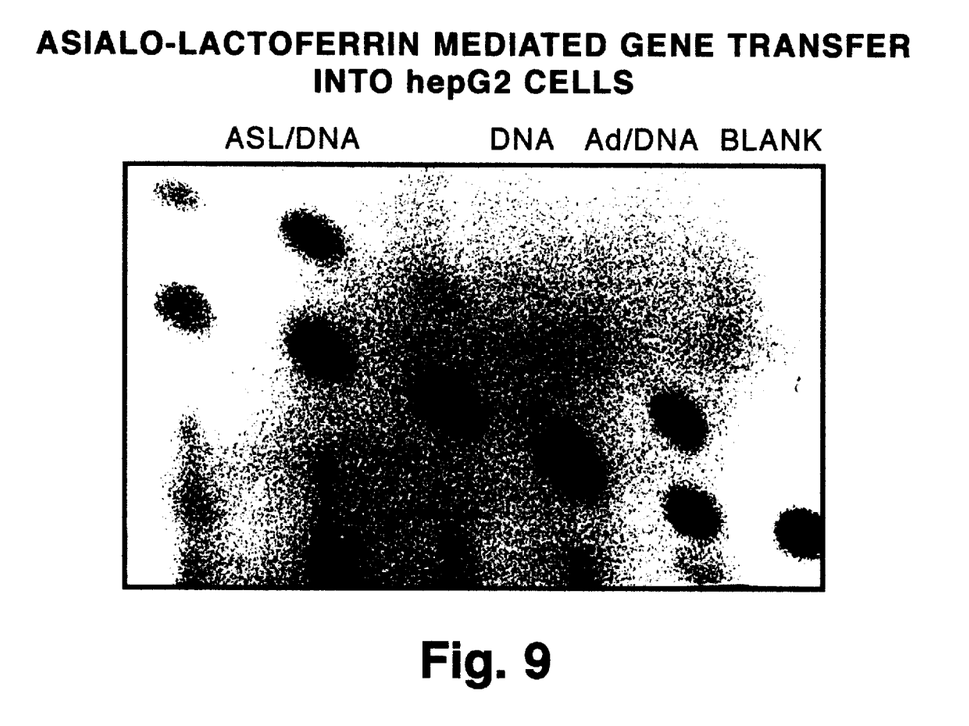
FIG. 9 shows Asialo-lactoferrin mediated gene transfer into hepG2 (hepatoma) cells.

HepG2 is a well differentiated cell line which is commonly used as a model for hepatocytes. HepG2 cells were exposed to a complex lactoferrin and DNA encoding the enzyme chloramphenicol acetyltransferase. The identical experiment was performed using a media which also contained non-infectious adenovirus particles. The presence of CAT activity in cells treated with LF/DNA indicates that the gene has been successfully transferred into these cells (see FIG. 8). There is greater activity in the presence of adenovirus which enhances the trafficking of materials out of the endosome after receptor mediated endocytosis. Control experiments (FIG. 9) demonstrate that there is no CAT activity in cells treated with DNA alone, lactoferrin alone, or adenovirus alone. CAT activity was evident in control experiments treated with DNA and adenovirus.

HepG2 cells were exposed to asialo-lactoferrin-DNA complexes in which the DNA encoded chloramphenicol acetyltransferase. The presence of CAT activity in cells treated with this complex but not DNA alone indicates that the gene has been successfully transferred into these cells.

EXAMPLE 12

Lactoferrin Mediated Gene Transfer Into So18 Cells (Myoblasts)

Figure 10:
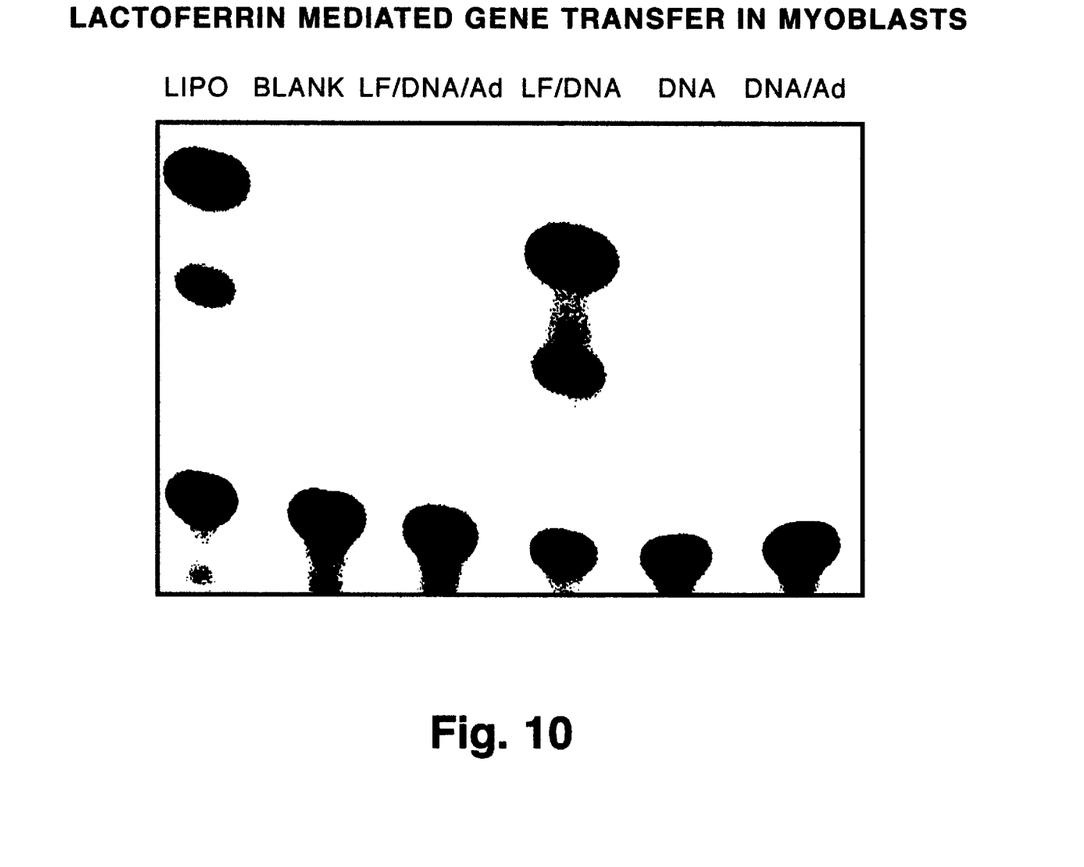
FIG. 10 shows lactoferrin mediated gene transfer into so18 cells (myoblasts).

So18 is a continuous myoblast line that exhibits many properties of myoblasts or myocytes including differentiation in culture. Cells were exposed to a vector encoding chloramphenicol acetyltransferase under different conditions (FIG. 10). CAT activity was measured in cells transfected using lipofectin™ (GIBCO) as a positive control, in cells exposed to media alone, in cells exposed to lactoferrin-DNA complex in media containing also adenovirus particles, in cells exposed to lactoferrin-DNA alone, in cells exposed to DNA alone, and in cells exposed to DNA in media containing also adenovirus. Adenovirus in the media was highly toxic to cells. The presence of CAT activity in cells exposed to lactoferrin-DNA complexes indicates that gene transfer into these cells is as efficient as lipofectin™.

All patents and publications mentioned in this specification are indicative of the levels of those skilled in the art to which the invention pertains. All patents an publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples of DNA vectors along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What we claim is:

1. A chimeric protein produced by a recombinant DNA technique from two domains of separate native proteins comprising:
   (a) a DNA-binding element selected from the group consisting of histone, nuclear hormone receptor, and transacting regulatory element, and
   (b) a ligand-binding element which binds to one or more specific receptors on the surface of target cells and is selected from the group consisting of protein hormone, glycoprotein hormone, immunoglobulin, serum protein, vitamin binding protein, transcobalamin I, transcobalamin II, R binder, intrinsic factor, cytokine, neuropeptide, and cell adhesion molecule.

2. The chimeric protein of claim 1, wherein:
   (a) said elements are combined to comprise a single chimeric recombinant molecule comprising a protein encoded by recombinant DNA; and
   (b) the order, spacing and orientation of said elements is appropriate for gene transfer.

3. The chimeric protein of claim 1, wherein said DNA-binding element is a histone.

4. The chimeric protein of claim 1, wherein said DNA-binding element is a nuclear hormone receptor.

5. The chimeric protein of claim 1, wherein said DNA-binding element is a transacting regulatory element.

6. The chimeric protein of claim 1, wherein said ligand-binding element is a protein hormone.

7. The chimeric protein of claim 1, wherein said ligand-binding element is a glycoprotein hormone.

8. The chimeric protein of claim 1, wherein said ligand-binding element is a vitamin binding protein.

9. The chimeric protein of claim 1, wherein said ligand-binding element is transcobalamin I.

10. The chimeric protein of claim 1, wherein said ligand-binding element is transcobalamin II.

11. The chimeric protein of claim 1, wherein said ligand-binding element is R binder.

12. The chimeric protein of claim 1, wherein said ligand-binding element is intrinsic factor.

13. The chimeric protein of claim 1, wherein said ligand-binding element is a cytokine.

14. The chimeric protein of claim 1, wherein said ligand-binding element is a neuropeptide.

15. The chimeric protein of claim 1, wherein said ligand-binding element is a cell adhesion molecule.

16. The chimeric protein of claim 1, wherein said ligand-binding element is not an immunoglobulin.

17. The chimeric protein of claim 1, wherein said ligand-binding element is not a serum protein.

18. A complex for gene transfer comprising:
   (a) a chimeric protein produced by a recombinant DNA technique from two domains of separate native proteins comprising a ligand binding element which binds to one or more specific receptors on the surface of target cells and a DNA-binding element selected from the group consisting of histone, nuclear hormone receptor, and transacting regulatory element; and (b) DNA bound nonspecifically to said DNA-binding element of said chimeric protein; wherein
said ligand-binding element is selected from the group consisting of protein hormone, glycoprotein hormone, immunoglobulin, serum protein, vitamin binding protein, transcobalamin I, transcobalamin II, R binder, intrinsic factor, cytokine, neuropeptide, and cell adhesion molecule.

19. The complex for gene transfer of claim 18, wherein:
(a) said DNA-binding element and said ligand element of said chimeric protein are combined to comprise a single chimeric recombinant molecule comprising a protein encoded by recombinant DNA; and
(b) the order, spacing and orientation of said elements is appropriate for gene transfer.

20. The complex for gene transfer of claim 18, wherein said DNA-binding element is a histone.

21. The complex for gene transfer of claim 18, wherein said DNA-binding element is a nuclear hormone receptor.

22. The complex for gene transfer of claim 18, wherein said DNA-binding element is a transacting regulatory element.

23. The complex for gene transfer of claim 18, wherein said ligand-binding element is a protein hormone.

24. The complex for gene transfer of claim 18, wherein said ligand-binding element is a glycoprotein hormone.

25. The complex for gene transfer of claim 18, wherein said ligand-binding element is a vitamin binding protein.

26. The complex for gene transfer of claim 18, wherein said ligand-binding element is transcobalamin I.

27. The complex for gene transfer of claim 18, wherein said ligand-binding element is transcobalamin II.

28. The complex for gene transfer of claim 18, wherein said ligand-binding element is R binder.

29. The complex for gene transfer of claim 18, wherein said ligand-binding element is intrinsic factor.

30. The complex for gene transfer of claim 18, wherein said ligand-binding element is a cytokine.

31. The complex for gene transfer of claim 18, wherein said ligand-binding element is a neuropeptide.

32. The complex for gene transfer of claim 18, wherein said ligand-binding element is a cell adhesion molecule.

33. The complex for gene transfer of claim 18, wherein said ligand-binding element is not an immunoglobulin.

34. The complex for gene transfer of claim 18, wherein said ligand-binding element is not a serum protein.

35. A carrier for gene transfer comprising a DNA-binding element and a ligand binding element, wherein the improvement consists of the carrier comprising a chimeric protein produced by a recombinant DNA technique from two domains of separate native proteins, wherein:

(a) said DNA-binding element is selected from the group consisting of histone, nuclear hormone receptor, and transacting regulatory element; and
(b) said ligand-binding element binds to one or more receptors or the surface of target cells and is selected from the group consisting of protein hormone, glycoprotein hormone, immunoglobulin, serum protein, vitamin binding protein, transcobalamin I, transcobalamin II, R binder, intrinsic factor, cytokine, neuropeptide, and cell adhesion molecule.

36. The carrier for gene transfer of claim 35, wherein:
(a) said DNA-binding element and said ligand binding element are combined to comprise a single chimeric recombinant molecule comprising a protein encoded by recombinant DNA; and
(b) the order, spacing and orientation of said elements is appropriate for gene transfer.

37. The carrier for gene transfer of claim 35, wherein said DNA-binding element is a histone.

38. The carrier for gene transfer of claim 35, wherein said DNA-binding element is a nuclear hormone receptor.

39. The carrier for gene transfer of claim 35, wherein said DNA-binding element is a transacting regulatory element.

40. The carrier for gene transfer of claim 35, wherein said ligand-binding element is a protein hormone.

41. The carrier for gene transfer of claim 35, wherein said ligand-binding element is a glycoprotein hormone.

42. The carrier for gene transfer of claim 35, wherein said ligand-binding element is a vitamin binding protein.

43. The carrier for gene transfer of claim 35, wherein said ligand-binding element is transcobalamin I.

44. The carrier for gene transfer of claim 35, wherein said ligand-binding element is transcobalamin II.

45. The carrier for gene transfer of claim 35, wherein said ligand-binding element is R binder.

46. The carrier for gene transfer of claim 35, wherein said ligand-binding element is intrinsic factor.

47. The carrier for gene transfer of claim 35, wherein said ligand-binding element is a cytokine.

48. The carrier for gene transfer of claim 35, wherein said ligand-binding element is a neuropeptide.

49. The carrier for gene transfer of claim 35, wherein said ligand-binding element is a cell adhesion molecule.

50. The carrier for gene transfer of claim 35, wherein said ligand-binding element is not an immunoglobulin.

51. The carrier for gene transfer of claim 35, wherein said ligand-binding element is not a serum protein.

* * * * *